(12) United States Patent
Everett et al.

(10) Patent No.: US 8,757,803 B2
(45) Date of Patent: Jun. 24, 2014

(54) VARIABLE RESOLUTION OPTICAL COHERENCE TOMOGRAPHY SCANNER AND METHOD FOR USING SAME

(71) Applicant: Carl Zeiss Meditec, Inc., Dublin, CA (US)

(72) Inventors: Matthew J. Everett, Livermore, CA (US); Keith E. O'Hara, San Ramon, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 0 days.

(21) Appl. No.: 13/903,797

(22) Filed: May 28, 2013

(65) Prior Publication Data

US 2013/0250241 A1  Sep. 26, 2013

Related U.S. Application Data

(62) Division of application No. 12/611,994, filed on Nov. 4, 2009, now Pat. No. 8,500,279.

(60) Provisional application No. 61/111,908, filed on Nov. 6, 2008.

(51) Int. Cl.
 *A61B 3/14* (2006.01)
 *A61B 3/10* (2006.01)

(52) U.S. Cl.
 CPC .. *A61B 3/102* (2013.01); *A61B 3/14* (2013.01)
 USPC ............................ 351/206; 351/246; 351/221

(58) Field of Classification Search
 CPC ....... A61B 3/102; A61B 3/14; G01B 9/02091
 USPC .......................................... 351/206, 246, 221
 See application file for complete search history.

(56) References Cited

U.S. PATENT DOCUMENTS

| | | | |
|---|---|---|---|
| 5,321,501 | A | 6/1994 | Swanson et al. |
| 5,459,570 | A | 10/1995 | Swanson et al. |
| 5,506,634 | A | 4/1996 | Wei et al. |
| 5,975,697 | A | 11/1999 | Podoleanu et al. |
| 6,549,801 | B1 | 4/2003 | Chen et al. |
| 6,769,769 | B2 | 8/2004 | Podoleanu et al. |
| 6,985,235 | B2 | 1/2006 | Bao et al. |
| 7,301,644 | B2 | 11/2007 | Knighton et al. |

(Continued)

FOREIGN PATENT DOCUMENTS

| | | |
|---|---|---|
| WO | 2010/006785 A1 | 1/2010 |
| WO | 2011/037980 A2 | 3/2011 |

OTHER PUBLICATIONS

An et al., "In vivo Volumetric Imaging of Vascular Perfusion within Human Retina and Choroids with Optical Micro-Angiography", Optics Express, vol. 16, No. 15, Jul. 21, 2008, pp. 11438-11452.

(Continued)

*Primary Examiner* — Zachary Wilkes
(74) *Attorney, Agent, or Firm* — Morrison & Foerster LLP

(57) ABSTRACT

The invention relates generally to optical tomographic imaging and in particular to systems and methods for adapting the resolution of imaging. One embodiment of the present invention is an apparatus for optical coherence tomography imaging, characterized by its ability to vary the axial resolution and scanning speed during imaging.

11 Claims, 3 Drawing Sheets

(56) References Cited

U.S. PATENT DOCUMENTS

| | | | |
|---|---|---|---|
| 7,330,270 | B2 | 2/2008 | O'Hara et al. |
| 7,342,659 | B2 | 3/2008 | Horn et al. |
| 7,359,062 | B2 | 4/2008 | Chen et al. |
| 7,375,818 | B2 | 5/2008 | Kawahara |
| 7,382,464 | B2 | 6/2008 | Everett et al. |
| 7,415,049 | B2 | 8/2008 | Flanders et al. |
| 7,505,142 | B2* | 3/2009 | Knighton et al. ............. 356/479 |
| 7,602,500 | B2 | 10/2009 | Izatt et al. |
| 7,692,797 | B2 | 4/2010 | Kawahara |
| 7,768,651 | B2 | 8/2010 | Ueno et al. |
| 7,864,335 | B2 | 1/2011 | Terakawa et al. |
| 7,884,945 | B2 | 2/2011 | Srinivasan et al. |
| 7,995,814 | B2 | 8/2011 | Fingler et al. |
| 2005/0190371 | A1 | 9/2005 | Knuttel |
| 2006/0066869 | A1 | 3/2006 | Ueno et al. |
| 2006/0164653 | A1* | 7/2006 | Everett et al. ................. 356/479 |
| 2007/0024856 | A1 | 2/2007 | Izatt et al. |
| 2007/0216909 | A1 | 9/2007 | Everett et al. |
| 2007/0276269 | A1 | 11/2007 | Yun et al. |
| 2008/0273783 | A1 | 11/2008 | Toth et al. |
| 2009/0046295 | A1 | 2/2009 | Kemp et al. |
| 2010/0110376 | A1 | 5/2010 | Everett et al. |
| 2010/0150422 | A1 | 6/2010 | Vakoc et al. |
| 2012/0277579 | A1 | 11/2012 | Sharma et al. |
| 2013/0120757 | A1 | 5/2013 | Yu et al. |

OTHER PUBLICATIONS

Blatter et al., "Ultrahigh-Speed Non-Invasive Widefield Angiography", Journal of Biomedical Optics, vol. 17, No. 7, Jul. 2012, pp. 070505-1-070505-3.

Fingler et al., "Mobility and Transverse Flow Visualization using Phase Variance Contrast with Spectral Domain Optical Coherence Tomography", Optics Express, vol. 15, No. 20, Oct. 1, 2007, pp. 12636-12653.

Fingler et al., "Volumetric Microvascular Imaging of Human Retina using Optical Coherence Tomography with a Novel Motion Contrast Technique", Optics Express, vol. 17, No. 24, Nov. 23, 2009, pp. 22190-22200.

Golubovic et al., "Optical Frequency-Domain Reflectometry using Rapid Wavelength Tuning of a Cr4+:Forsterite Laser", Optics Letters, vol. 22, No. 22, Nov. 15, 1997, pp. 1704-1706.

Gora et al., "Ultra High-Speed Swept Source OCT Imaging of the Anterior Segment of Human Eye at 200 kHz with Adjustable Imaging Range", Optics Express, vol. 17, No. 17, Aug. 17, 2009, pp. 14880-14894.

Huber et al., "Amplified, Frequency Swept Lasers for Frequency Domain Reflectometry and OCT Imaging: Design and Scaling Principles", Optics Express, vol. 13, No. 9, May 2, 2005, pp. 3513-3528.

Jia et al., "Split-Spectrum Amplitude-Decorrelation Angiography with Optical Coherence Tomography", Optics Express, vol. 20, No. 4, Feb. 13, 2012, pp. 4710-4725.

Kim et al., "In vivo Volumetric Imaging of Human Retinal Circulation with Phase-Variance Optical Coherence Tomography", Biomedical Optics Express, vol. 2, No. 6, Jun. 1, 2011, pp. 1504-1513.

Klein et al., "Multi-MHz FDML OCT: Snapshot Retinal Imaging at 6.7 Million Axial-Scans Per Second", Proc. of SPIE, vol. 8213, 2012, pp. 82131E-1-82131E-6.

Kourogi et al., "Programmable High Speed (~1MHz) Vernier-Mode-Locked Frequency- Swept Laser for OCT Imaging", Proc. of SPIE, vol. 6847, 2008, pp. 68470Z-1-68470Z-8.

Lee et al., "Wide Tuning Range Wavelength-Swept Laser with a Single SOA at 1020 nm for Ultrahigh Resolution Fourier-Domain Optical Coherence Tomography", Optics Express, vol. 19, No. 22, Oct. 24, 2011, pp. 21227-21237.

Lee, Sang-Won, "Optimization for Axial Resolution, Depth Range, and Sensitivity of Spectral Domain Optical Coherence Tomography at 1.3 μm", Journal of the Korean Physical Society, vol. 55, No. 6, Dec. 2009, pp. 2354-2360.

Makita et al., "Optical Coherence Angiography", Optics Express, vol. 14, No. 17, Aug. 21, 2006, pp. 7821-7840.

Mariampillai et al., "Optimized Speckle Variance OCT Imaging of Microvasculature", Optics Letters, vol. 35, No. 8, Apr. 15, 2010, pp. 1257-1259.

International Search Report and Written Opinion received for PCT Patent Application No. PCT/EP2012/050796, mailed on Apr. 27, 2012, 11 pages.

Podoleanu et al., "OCT En-Face Images from the Retina with Adjustable Depth Resolution in Real Time", IEEE Journal of Selected Topics in Quantum Electronics, vol. 5, No. 4, Jul./Aug. 1999, pp. 1176-1184.

Wang et al., "Three Dimensional Optical Angiography", Optics Express, vol. 15, No. 7, Apr. 2, 2007, pp. 4083-4097.

Xi et al., "Evaluation of Spectrometric Parameters in Spectral-Domain Optical Coherence Tomography", Applied Optics, vol. 50, No. 3, Jan. 20, 2011, pp. 366-372.

Xi et al., "Generic Real-time Uniform K-Space Sampling Method for High-Speed Swept-Source Optical Coherence Tomography", Optics Express, vol. 18, No. 9, Apr. 26, 2010, pp. 9511-9517.

Yasuno et al., "Three-Dimensional and High-Speed Swept-Source Optical Coherence Tomography for in Vivo Investigation of Human Anterior Eye Segments", Optics Express, vol. 13, No. 26, Dec. 26, 2005, pp. 10652-10664.

Yun et al., "High-Speed Optical Frequency Domain Imaging", Optics Express, vol. 11, No. 22, Nov. 3, 2003, pp. 2953-2963.

Zhang et al., "Swept Laser Source at 1 μm for Fourier Domain Optical Coherence Tomography", Applied Physics Letters, vol. 89, 2006, pp. 073901-1-073901-3.

Non-Final Office Action received for U.S. Appl. No. 12/611,994, mailed on Apr. 14, 2011, 14 pages.

Final Office Action received for U.S. Appl. No. 12/611,994, mailed on Oct. 3, 2011, 13 pages.

Notice of Allowance received for U.S. Appl. No. 12/611,994, mailed on Dec. 22, 2011, 8 pages.

Non Final Office Action received for U.S. Appl. No. 12/611,994, mailed on Oct. 18, 2012, 13 pages.

Notice of Allowance received for U.S. Appl. No. 12/611,994, mailed on Feb. 22, 2013, 8 pages.

Fujimoto et al., "Optical Coherence Tomography: An Emerging Technology for Biomedical Imaging and Optical Biopsy", Neoplasia, vol. 2, No. 1-2, Jan.-Apr. 2000, pp. 9-25.

Fercher et al., "Optical Coherence Tomography-Principles and Applications", Reports on Progress in Physics, vol. 66, 2003, pp. 239-303.

Huang et al., "Optical Coherence Tomography", Science, vol. 254, Nov. 22, 1991, pp. 1178-1181.

Leitgeb et al., "Spectral Measurement of Absorption by Spectroscopic Frequency-domain Optical Coherence Tomography", Optics Letters, 2000, pp. 820-822.

Leitgeb et al., "Performance of Fourier Domain vs. Time Domain Optical Coherence Tomography", Optics Express vol. 11, No. 8, Apr. 21, 2003, pp. 889-894.

Leitgeb et al., "Ultrahigh Resolution Fourier Domain Optical Coherence Tomography", Optics Express, vol. 12, No. 10, May 17, 2004, pp. 2156-2165.

Lee et al., "In vivo Optical Frequency Domain Imaging of Human Retina and Choroid", Optics Express, vol. 14, No. 10, May 15, 2006, pp. 4403-4411.

Považay et al., "High-Speed High-Resolution Optical Coherence Tomography at 800 and 1060 nm", Proceedings of the SPIE, vol. 7139, 2008, 7 pages.

Rollins et al., "Emerging Clinical Applications of Optical Coherence Tomography", Optics and Photonics News, vol. 13, No. 4, Apr. 2002, pp. 36-41.

Schmitt, Joseph M., "Optical Coherence Tomography (OCT): A Review", IEEE Journal of Selected Topics in Quantum Electronics, vol. 5, No. 4, Jul./Aug. 1999, pp. 1205-1215.

Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.

(56) References Cited

OTHER PUBLICATIONS

Barfuss et al., "Modified Optical Frequency Domain Reflectometry with High Spatial Resolution for Components of Integrated Optic Systems", Journal of Lightwave Technology, vol. 7, No. 1, Jan. 1989, pp. 3-10.

Choma et al., "Sensitivity Advantage of Swept Source and Fourier Domain Optical Coherence Tomography", Optics Express, vol. 11, No. 18, Sep. 8, 2003, pp. 2183-2189.

Eickhoff et al., "Optical Frequency Domain Reflectometry in Single-Mode Fiber", Applied Physics Letters, vol. 39, No. 9, Nov. 1, 1981, pp. 693-695.

Fujimoto, James G., "Optical Coherence Tomography for Ultrahigh Resolution in Vivo Imaging", Nature Biotechnology, vol. 21, No. 11, Nov. 2003, pp. 1361-1367.

Lexer et al., "Wavelength-Tuning Interferometry of Intraocular Distances", Applied Optics, vol. 36, No. 25, Sep. 1, 1997, pp. 6548-6552.

Yun et al., "Motion Artifacts in Optical Coherence Tomography with Frequency-Domain Ranging", Optics Express, vol. 12, No. 13, Jun. 28, 2004, pp. 2977-2998.

Yun et al., "Removing the Depth-Degeneracy in Optical Frequency Domain Imaging with Frequency Shifting", Optics Express, vol. 12, No. 20, Oct. 4, 2004, pp. 4822-4828.

* cited by examiner

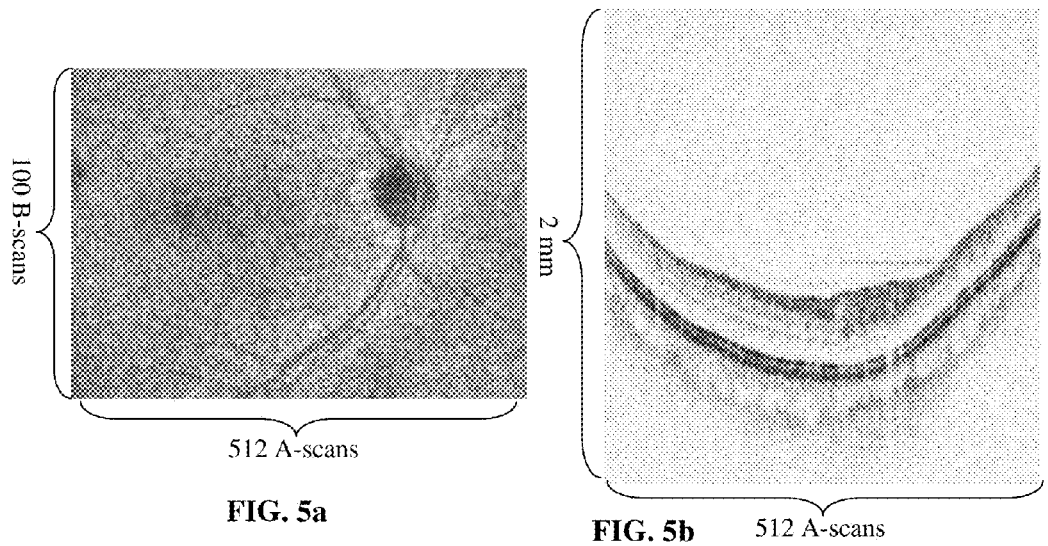
FIG. 5a
FIG. 5b
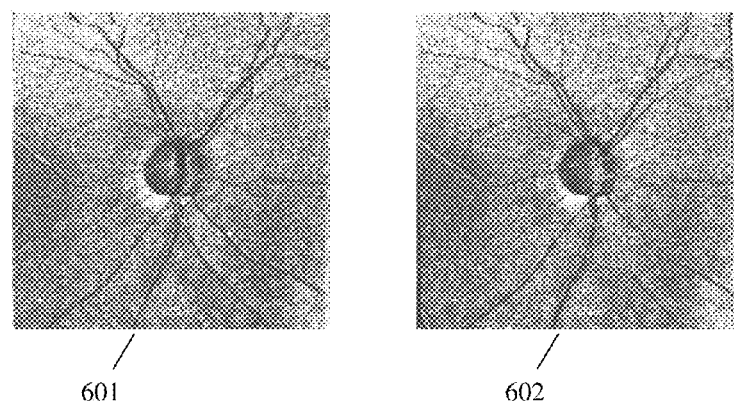
FIG. 6a
FIG. 6b

VARIABLE RESOLUTION OPTICAL COHERENCE TOMOGRAPHY SCANNER AND METHOD FOR USING SAME

PRIORITY

This application is a divisional of U.S. patent application Ser. No. 12/611,994, filed Nov. 4, 2009, which in turn claims the benefit of the filing date under 35 U.S.C. §119(e) of Provisional U.S. Patent Application Ser. No. 61/111,908, filed on Nov. 6, 2008, which is hereby incorporated by reference in its entirety.

TECHNICAL FIELD

The invention relates generally to optical tomographic imaging and in particular to systems and methods for adapting the resolution of imaging.

BACKGROUND

Optical coherence tomography (OCT) has been widely and successfully used in the imaging of biological tissues (Huang, D., E. A. Swanson, et al. (1991). "Optical coherence tomography." Science 254 (5035): 1178-81; and U.S. Pat. Nos. 5,321,501 and 5,459,570). A large of number of applications have been found for this technology as evidenced by a number of review articles [Swanson E. A. et al. "Optical coherence tomography, Principles, instrumentation, and biological applications" in *Biomedical Optical Instrumentation and Laser-Assisted Biotechnology*, A. M. Verga Scheggi et al. (eds.) pages: 291-303, 1996 Kluwer Academic Publishers, Printed in the Netherlands; Schmitt, J. M. "Optical coherence tomography (OCT): a review" *IEEE Journal of Selected Topics in Quantum Electronics* 5(4):1205-1215 (1999); Fujimoto, J. G. et al. "Optical Coherence Tomography: An Emerging Technology for Biomedical Imaging and Optical Biopsy" *Neoplasia* 2:9-25 (2000); Rollins A. M. et al. "Emerging Clinical Applications of Optical Coherence Tomography" *Optics and Photonics News* 13(4): 36-41 (2002); Fujimoto, J. G. "Optical coherence tomography for ultrahigh resolution in vivo imaging." *Nature Biotechnology* 21(11): 1361-7 (2003)].

Descriptions of the modern use of OCT in ophthalmology are given by Wojtkowski, et al., [*Ophthalmology* 112(10): 1734 (2005)] and by Lee et al. [*Optics Express* 14(10):4403 (2006).]

The publications and patents cited above as well as those cited throughout this patent application are incorporated herein by reference.

To make a clinically useful device, in ophthalmology, typically OCT is used in conjunction with a fundus viewer, [User Manual for the Zeiss OCT Model 3000 pp. 3-1 to 3-4 and p. 9-1, U.S. No. Pat. 5,506,634] or with a scanning laser ophthalmoscope (SLO) [U.S. Pat. Nos. 6,769,769 and 7,382,464]. These secondary devices provide a live view of the retina, this live view being en-face (from the front) as opposed to tomographic (in cross-section), for use in correctly placing the OCT scan so the tomograms are acquired at the locations of interest. As technology has advanced, OCT systems are now fast enough to collect axial scans over a two-dimensional transverse extent of the retina, resulting in three dimensional data volumes, which are acquired within the time a patient can comfortably keep his eye open and steady. These volume scans can be processed to give a useful high-contrast en-face view [U.S. Pat. No. 7,301,644]. This process would enable a live en-face view from the OCT scanner alone, without the secondary fundus viewing system, if the rate of en-face views were fast enough.

Thus there would be utility, in at least the field of ophthalmology, for an OCT scanner that can be quickly re-configured to trade speed for axial resolution, allowing a mode of operation sufficiently fast to practically replace the fundus viewer with an en-face image derived from an OCT volume.

SUMMARY

The present invention is defined by the claims and nothing in this section should be taken as a limitation on those claims.

One aspect of the present invention is to permit the rapid generation of a live en-face view from the OCT scanner alone, eliminating the need for a secondary fundus viewing system. The acquisition rate is improved by trading axial resolution for increased acquisition speed so that the OCT system provides en-face views sufficiently rapidly that a secondary fundus viewing system is not needed. The en-face rendering sums the acquired OCT data along an axial segment and contains only a single pixel representing the entire axial length over which the data is summed. When used merely to create en-face images, the typical high level of axial resolution available from the OCT system is not needed. Its high sensitivity to returned light, however, is very helpful in creating bright images while exposing the subject to only low levels of illumination light.

In one aspect of the present invention, a method and apparatus is provided for imaging a sample (in our preferred instance, a subject) in a manner capable of trading acquisition speed for axial resolution in an OCT system.

One embodiment of the present invention is a swept-source OCT system having a diagnostic mode and a set-up mode, wherein the extent of the spectral sweep of the light source used to generate the image of the eye during the set-up mode is about one half or less than the extent of the sweep of the light source used to generate the image of the eye during the diagnostic mode, such that the images in the set-up mode have a lower resolution than the images in the diagnostic mode but can be rendered in a shorter period of time.

Another embodiment of the present invention is OCT is a spectral-domain OCT system having a diagnostic mode and a set-up mode, wherein the number of detectors elements used to record the interference spectra that generate the image of the eye during the set-up mode, is about one half or less than the number of detector elements used during the diagnostic mode. Again, the images in the set-up mode have a lower axial resolution than the images in the diagnostic mode but can be rendered in a shorter period of time.

In both embodiments, the spectral range acquired during the set-up mode is less than the spectral range acquired during the diagnostic mode. Further, the data acquired across the spectral range acquired during the set-up mode comprises fewer data elements than the data acquired during the diagnostic mode. Further, the number of sampled wavelengths used to generate the image of the eye during the set-up mode is less than the number of sampled wavelengths used to generate the image of the eye during the diagnostic mode.

BRIEF DESCRIPTION OF THE DRAWINGS

FIG. 3A is a schematic illustration of the reflectivity versus depth derived from the full interference spectrum of FIG. 2 while

FIGS. 5A and 5B shows an en-face view and exemplary tomogram respectively taken from an OCT data volume using only a portion of the range as was used for FIG. 4

FIGS. 6A and 6B shows a stereo pair derived from a single OCT data volume

DETAILED DESCRIPTION

Figure 1:
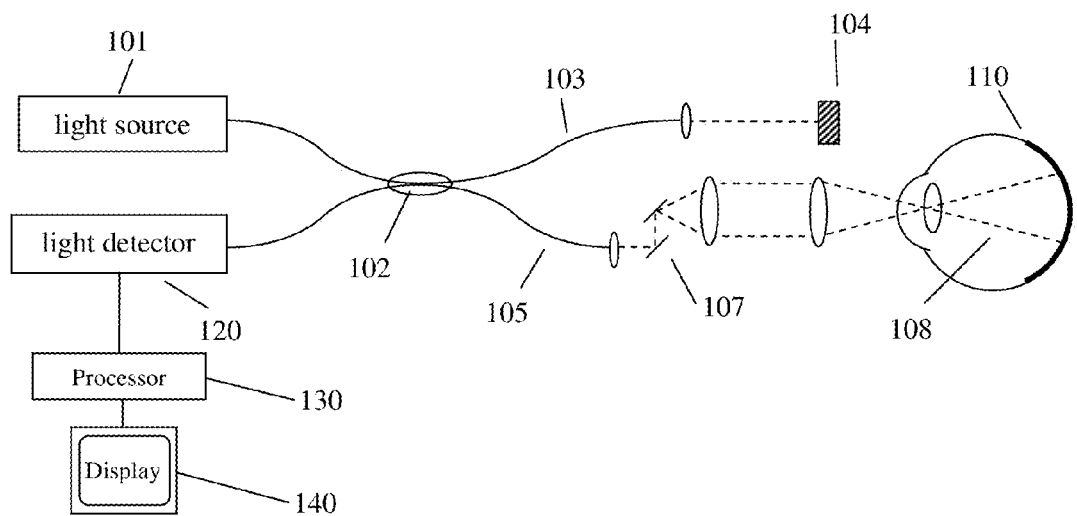
FIG. 1 is a schematic illustration of an optical coherence tomography (OCT) scanner.

An optical coherence tomography scanner, illustrated in FIG. 1 typically includes a spatially coherent source of light, 101. This source can be either a broadband light source with short temporal coherence length or a swept laser source. (See for example, respectively, Wojtkowski, et al., [*Ophthalmology* 112(10):1734 (2005)] or Lee et al. [*Optics Express* 14(10):4403 (2006)].)

Light from source 101 is routed, typically by optical fiber 105, to illuminate the sample 110, a typical sample being tissues at the back of the human eye. The light is scanned, typically with a scanner 107 between the output of the fiber and the sample, so that the beam of light (dashed line 108) sweeps over the area or volume to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form interfered light which is routed to a detector 120. The output from the detector is supplied to a processor 130. The results can be stored in the processor or displayed on display 140.

The interference causes the intensity of the interfered light to vary across the spectrum. For any scattering point in the sample, there will be a certain difference in the path length between light from the source and reflected from that point, and light from the source traveling the reference path. The interfered light has an intensity that is relatively high or low depending on whether the path length difference is an even or odd number of half-wavelengths, as these path length differences result in constructive or destructive interference respectively. Thus the intensity of the interfered light varies with wavelength in a way that reveals the path length difference; greater path length difference results in faster variation between constructive and destructive interference across the spectrum. The Fourier transform of the interference spectrum reveals the profile of scattering intensities at different path lengths, and therefore scattering as a function of depth in the sample [see for example, Leitgeb et al, *Optics Express* 12(10):2156 (2004)].

The profile of scattering as a function of depth is called an axial scan (A-scan). A set of A-scans measured at neighboring locations in the sample produces a cross-sectional image (tomogram) of the sample.

The range of wavelengths at which the interference is recorded determines the resolution with which one can determine the depth of the scattering centers, and thus the axial resolution of the tomogram. We define the spatial optical frequency, $q=2\pi n/\lambda$, for light with wavelength $\lambda$ in a sample having mean index of refraction n. The relation between range of recorded optical frequencies, $\Delta q$, and axial resolution $\Delta z$, is then $\Delta z = 4 \ln 2/\Delta q$. Recording a limited range of optical frequencies results in coarser axial resolution. If we build a system in which a limited range of optical frequencies can be recorded and processed more quickly than the full range, the system is then able to trade imaging speed for imaging resolution.

Figure 2:
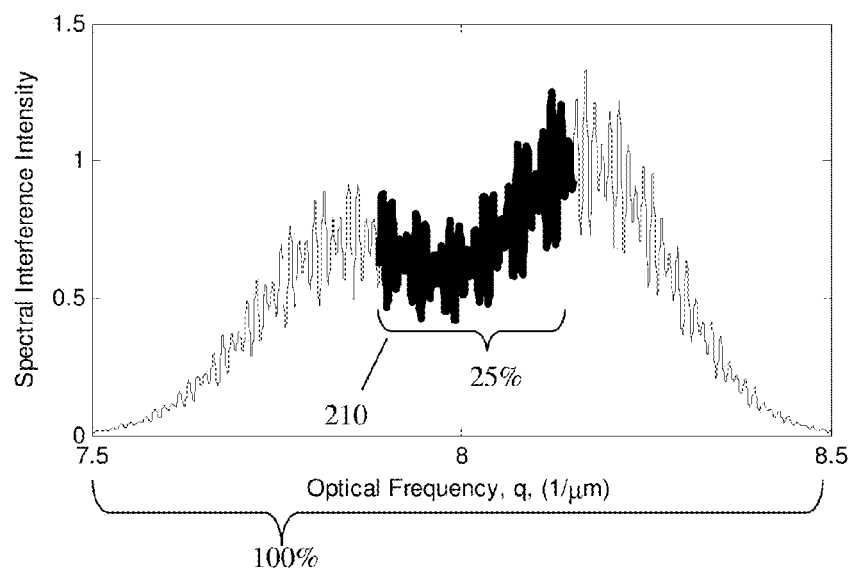
FIG. 2 is a schematic illustration of an interference spectrum from which depth-dependent reflectivity is determined in an OCT scanner.
Figure 3A:
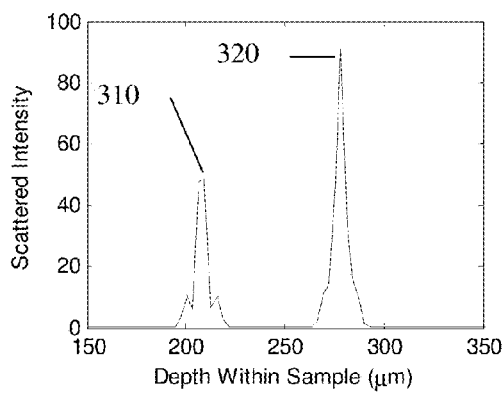
Figure 3B:
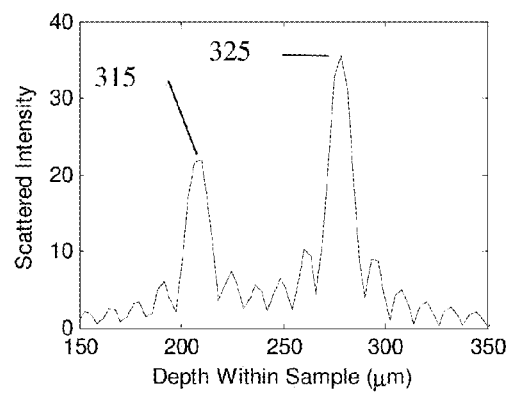
FIG. 3B is an illustration of reflectivity versus depth derived from the partial interference spectrum of FIG. 2

FIG. 2 represents an interference spectrum collected with two scattering centers in the sample reflecting light back to the system. The darkened region 210 represents 25% of the effective spectral range. If the full spectrum is recorded and Fourier transformed, the resulting A-scan is represented by a curve like the curve plotted in FIG. 3a, plotting scattered intensity versus depth. In this example, the two scattering centers create two peaks, 310 and 320, in the intensity versus depth. If only the central 25% of the spectrum is recorded and Fourier transformed, we see the resulting A-scan plotted in FIG. 3b, which shows the reduced axial resolution in the associated peaks, 315 and 325. (Optionally, an apodization window can be used in the processing to smooth out the side-lobes seen in FIG. 3b, as is often done before Fourier transforms.)

Embodiment Using Spectral Domain (SD) Optical Coherence Tomography (OCT)

The detection path in a spectral-domain embodiment includes a camera to record the dispersed interference spectra. Each spectrum contains the information used to create an A-scan. The camera is chosen to be capable of detecting and electronically transmitting either the entire spectrum or just a portion of the spectrum, preferably the middle portion of the spectrum. Then, for a constant data transfer rate, in pixels per second, one can trade spectral bandwidth for the total time required to read the spectra from the camera, in A-scans per second.

A preferred camera for measuring the spectra is a CMOS line array camera with 2048 pixels that can convert and transmit pixel data at 140 million pixels per second (140 MP/s) either from the whole camera array or a portion of the camera array.

In an ophthalmic imaging application, the person operating the OCT scanner benefits greatly from a real-time view of the OCT image while aligning to the patient's eye, correcting for the patient's refractive error, setting the OCT imaging depth appropriate for the patient's eye length, and finding a region of the retina to be imaged. In the prior art, this is accomplished through a separate fundus viewer. In the present invention, this is accomplished by enabling a fast en-face mode within the OCT imager. In one instance of the spectral-domain embodiment, the camera is set to transmit the central 512 pixels only, at a rate of 200,000 A scans per second (200 k A-scan/s), which corresponds to a pixel rate of 100 MP/s, well within the capabilities of the preferred camera. If the full spectrum gives an axial resolution of 5 µm, typical for retinal imaging, then using this central portion amounting to 25% of the spectrum results in a lower axial resolution of about 20 µm. This level of axial resolution is sufficient for generating an en-face image for patient alignment. Preferably, but not necessarily, the spectrum of the illumination source is narrowed in this mode of operation, so that the patient is not exposed to light outside the spectrum that will be used for imaging. This can be accomplished by filtering the source or using an alternate source or by other means. The OCT beam is preferably scanned across a 25°×35° field-of view, so as to allow imaging of both the fovea centralis and optic disc. This field is preferably scanned using 100 lines (B-scans) each consisting of 512 A-scans. The 200 k A-scan/s rate of the detector allows presentation of this field at 4 frames per second. Preferably, an en-face image of the entire field is shown, plus one or more tomograms for setting the depth range, as illustrated in FIGS. 5A and 5B.

During this alignment method, the 20 μm axial resolution is sufficient for generation of useful stereoscopic pairs, as in FIGS. 6A and 6b, by projecting en-face images from the three-dimensional OCT data block along two directions. Note that the binocular separation angle between these viewing directions is not limited by the size of the patient's pupil, as it would be in stereo fundus photography; the angle can be chosen freely and the stereo images generated numerically from the three-dimensional volume of scattering intensity. This means that stereoscopic fundus images, familiar to the clinician from fundus photography through a dilated pupil, can be created from OCT images through a pupil without requiring dilation.

Figure 4A:
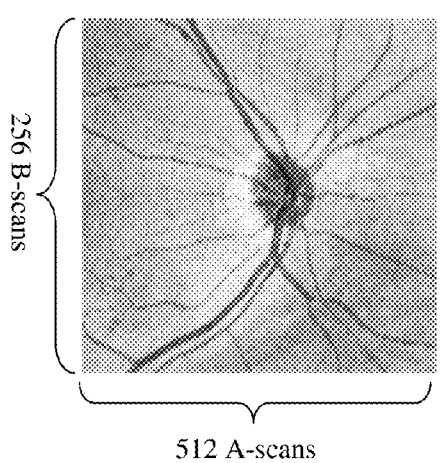
FIGS. 4A and 4B show an en-face view and exemplary tomogram respectively taken from an OCT data volume of the eye.
Figure 4B:
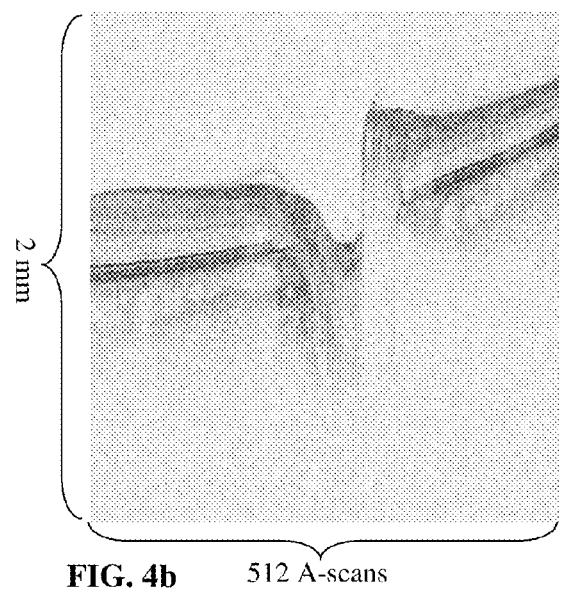

When the desired region is found, the operator initiates an image capture. (This may be accomplished by pressing a button, footswitch, touchpad, mouse or other user interface input.) If the illumination source bandwidth was narrowed for lower resolution scanning, it is returned to its full bandwidth and the image capture operation sets the camera to transmit all 2048 pixels at 70 k A-scan/s. Within 2 seconds, during which patients can reasonably hold the eye still and open for imaging, the scanner can capture a detailed block comprising preferably 512×256 A-scans covering a 20°×20° field of view, now with the full axial resolution, 5 μm for example, enabled by using the information in the full spectrum. An en-face image and tomogram from such a higher resolution scan are illustrated in FIGS. 4A and 4B. This detailed block is saved. Alternatively, a partial volume can be acquired, or one or more high density B-scans can be acquired where more than 512 A-scans are acquired more densely space as described in U.S. Publication No. 2007/0216909.

The device preferably also saves the final data block from the alignment operation, because the lower-resolution but wider field-of-view gives useful context for the location of the detailed block, particularly useful for registering image data between patient examinations over the course of medical monitoring and treatment as described in U.S. Publication No. 2007/0216909.

Embodiment Using Swept Source (SS) Optical Coherence Tomography (OCT)

A swept-source embodiment of the invention uses the same concept, but allows additional flexibility so it is the preferred embodiment whenever appropriate manufactured swept-sources are available.

The swept-source must be capable of sweeping over a full spectral range sufficient to produce OCT images with the required resolution, 40 THz spectral range to produce 5 μm resolution, for example. The laser is designed for a relatively fast rate of sweep of the lasing optical frequency, 4 THz/μs for example.

During patient alignment, the full resolution is not required, so the laser is swept over a more limited spectral range, preferably around one-quarter full capability of the laser, 10 THz for example. If we keep the rate of sweep at the design value, 4 THz/μs for example, then the laser dynamics stay the same, resulting in consistent power output and coherence length between alignment and capture modes. Each sweep through the spectrum requires 2.5 μs in this mode of operation. Allowing a typical dead time of 2.5 μs between sweeps, the rate of sweeps through the reduced spectral range is 200 k A-scan/s.

The full 40 THz spectrum is swept in 10 μs, so allowing now 4 μs dead time the system provides 70 k A-scan/s at full axial resolution. The sampling rate, in digitized samples per second of the interference signal, preferably remains the same between acquisition and capture modes of operation, so that the density of samples in optical frequency and the resulting depth range of the image remain the same between modes. Often an auxiliary interferometer is used to generate a sampling clock at equally spaced optical frequencies. Whether the digitization is clocked by an auxiliary interferometer or by an electronic clock, the consistent sweep rate between the two modes of operation produces a consistent data rate samples to the electronics performing image reconstruction.

The method of use of the instrument by the operator is the same as described earlier for the spectral-domain implementation.

Alternatives

Some tuning elements used in rapidly swept lasers are mechanical (U.S. Pat. Nos. 6,985,235 and 7,415,049 for example). The mechanical resonant frequencies of the tuning element can reasonably be expected to limit the cycle rate of the tuning element, given the desired cycle rates of 70 k to 200 k A-scan/s. A modification of the system described above can use a single cycle rate, 70 k A-scans/s for example.

During patient alignment the sweep rate can be reduced to 1 THz/μs and the sweep range reduced to 10 THz, maintaining 70 k A-scans/s. The rate of sweep is reduced to about 1 THz/μs so one should expect different laser dynamics than when sweeping the full spectral range. Specifically, higher output power and longer coherence length can be expected. The output power can usually be reduced by reducing electrical power provided to the gain medium. The rate of sampling and digitization of the interference signal is preferably the same as used for digitization of the full spectra, so during patient alignment with this alternative embodiment the samples will be more densely spaced in optical frequency. The greater sampling density and longer coherence length together provide a greater depth range in the resulting OCT images, as is well understood in the art of Fourier Domain OCT. The greater field of view in depth is advantageous during alignment of the patient.

The scan of the OCT beam during patient alignment covers preferably a 25°×35° field-of view, but with the lower cycle rate the A-scan density can be only 256×128 to generate en-face images and tomograms at 2 frames per second.

To some degree, transverse information can be encoded in the interference fringes within a single frequency sweep, if the beam scans significantly during one A-scan. The root-mean-square fringe amplitude can be extracted from the interference spectra to determine the reflectance at the current transverse location (as in U.S. Pat. No. 7,301,644). If transverse location changes significantly during the frequency sweep, en-face reflectivity at a range of locations can be extracted from a single A-scan.

It is convenient to call OCT methods such as SD-OCT or SS-OCT that employ frequency domain methods for acquiring and/or analyzing OCT data Frequency Domain (FD) Optical Coherence Tomography (OCT).

It should be understood that the embodiments, examples and descriptions have been chosen and described in order to illustrate the principles of the invention and its practical applications and not as a definition of the invention. Modifications and variations of the invention will be apparent to those skilled in the art. For instance, the extra scanning speed of the reduced resolution mode could also be used to generate a fundus image with greater transverse resolution in a given acquisition time relative to the high axial resolution imaging. The scope of the invention is defined by the claims, which includes known equivalents and unforeseeable equivalents at the time of filing of this application.

The following are hereby incorporated herein by reference.
U.S. Patent Documents
- U.S. Pat. No. 5,321,501, Swanson, Method and apparatus for optical imaging with means for controlling the longitudinal range of the sample
- U.S. Pat. No. 5,459,570, Swanson, Method and apparatus for performing optical measurements
- U.S. Pat. No. 5,506,634, Wei, Fundus illumination apparatus formed from three, separated radiation path systems
- U.S. Pat. No. 6,769,769, Podoleanu, Optical mapping apparatus with adjustable depth resolution and multiple functionality
- U.S. Pat. No. 6,985,235, Bao, Cascaded fiber Fabry-Perot filters
- U.S. Pat. No. 7,301,644, Knighton, Enhanced optical coherence tomography for anatomical mapping
- U.S. Pat. No. 7,330,270, O'Hara, Method to suppress artifacts in frequency-domain OCT
- U.S. Pat. No. 7,342,659, Horn, Cross-dispersed spectrometer in a spectral domain optical coherence tomography system
- U.S. Pat. No. 7,382,464, Everett, Apparatus and method for combined optical-coherence-tomographic and confocal detection
- U.S. Pat. No. 7,415,049, Flanders, Laser with tilted multi spatial mode resonator tuning element U.S. Patent Publication Documents
- 2007/0216909, Everett et al., Methods for Mapping Tissue with Optical Coherence Tomography Data Other Publications
- Leitgeb, R. A., et al. (2003). "Performance of Fourier domain vs. time domain optical coherence tomography." *Optics Express* 11(8): 889-894.

What is claimed is:

1. A swept-source optical coherence tomography (SS-OCT) system generating images of the eye comprising:
a light source for generating a probe beam designed to sweep a bandwidth of optical frequencies;
optics for scanning the beam across the eye;
a detector for measuring light returned from the eye; and,
a processor for generating images of the eye based on the output of the detector over a sampling of frequencies, said SS-OCT system having a first mode and a second mode, wherein the variation in wavelength per unit time is the same for both modes so that the sampling densities in both modes are the same but wherein the number of sampled frequencies used to generate the image of the eye during the second mode is less than the number of sampled frequencies used to generate the image of the eye during the first mode such that the images in the first mode have a different axial resolution than the images in the second mode.

2. A system as recited in claim 1, wherein the image generated during the second mode is created from a subset of the optical frequencies used to generate the image in the first mode.

3. A system as recited in claim 1, wherein the range of sampled frequencies is generated by opto-mechanical means.

4. A swept-source optical coherence tomography (SS-OCT) system generating images of the eye comprising:
a tunable light source for generating a probe beam;
optics for scanning the beam across the eye;
a detector for measuring light returned from the eye; and,
a processor for generating images of the eye based on the output of the detector;
said OCT system having two modes and the extent of the sweep of the light source used to generate the image of the eye during the second mode is less than the extent of the sweep of light source used to generate the image of the eye during the first mode and wherein the variation in wavelength per unit time is the same for both modes so that the sampling densities in both modes are the same.

5. A system as recited in claim 4, wherein the extent of the sweep of the light source used to generate the image of the eye during the second mode is one half or less than the extent of the sweep of light source used to generate the image of the eye during the first mode.

6. A system as recited in claim 5, wherein the image from the second mode is an en-face image.

7. A system as recited in claim 4, wherein the image from the second mode is an en-face image.

8. A system as recited in claim 4, wherein the image from the second mode is used as a set-up image, and image from the first mode is used as a diagnostic image.

9. A swept-source optical coherence tomography (SS-OCT) system generating images of the eye comprising:
a light source for generating a probe beam designed to sweep a bandwidth of optical frequencies;
optics for scanning the beam across the eye at multiple locations in an X/Y plane;
a detector for measuring light reflected from the eye; and,
a processor for generating images of the eye based on the output of the detector over a sampling of wavelengths;
said processor being operable to change both the scanning speed and the axial resolution of the generated images and wherein the axial resolution is changed by changing the number of optical frequencies used to generate the image, wherein in a first mode, the scanning speed is increased and the axial resolution is reduced and wherein in a second mode, the scanning speed is reduced and the axial resolution is increased and wherein during the first mode, the processor generates an en face image and wherein during the second mode, the processor generates a diagnostic image for evaluating the eye.

10. A system as recited in claim 9, wherein the axial resolution is changed by the sweep range.

11. A system as recited in claim 9, wherein the range of sample wavelengths is generated by opto-mechanical means.

* * * * *

UNITED STATES PATENT AND TRADEMARK OFFICE
CERTIFICATE OF CORRECTION

PATENT NO.            : 8,757,803 B2                                      Page 1 of 1
APPLICATION NO.  : 13/903797
DATED                     : June 24, 2014
INVENTOR(S)          : Matthew J. Everett et al.

It is certified that error appears in the above-identified patent and that said Letters Patent is hereby corrected as shown below:

In the Specification

In column 3, line 4, delete "2" and insert -- 2. --, therefor.

In column 3, line 10, delete "4" and insert -- 4. --, therefor.

In column 3, line 12, delete "volume" and insert -- volume. --, therefor.

In column 4, line 56, delete "Preferrably," and insert -- Preferably, --, therefor.

Signed and Sealed this
Twenty-third Day of September, 2014

Michelle K. Lee
*Deputy Director of the United States Patent and Trademark Office*